May 3, 1955 H. C. SWIM Plant Pat. 1,390
ROSE PLANT
Filed Aug. 23, 1954
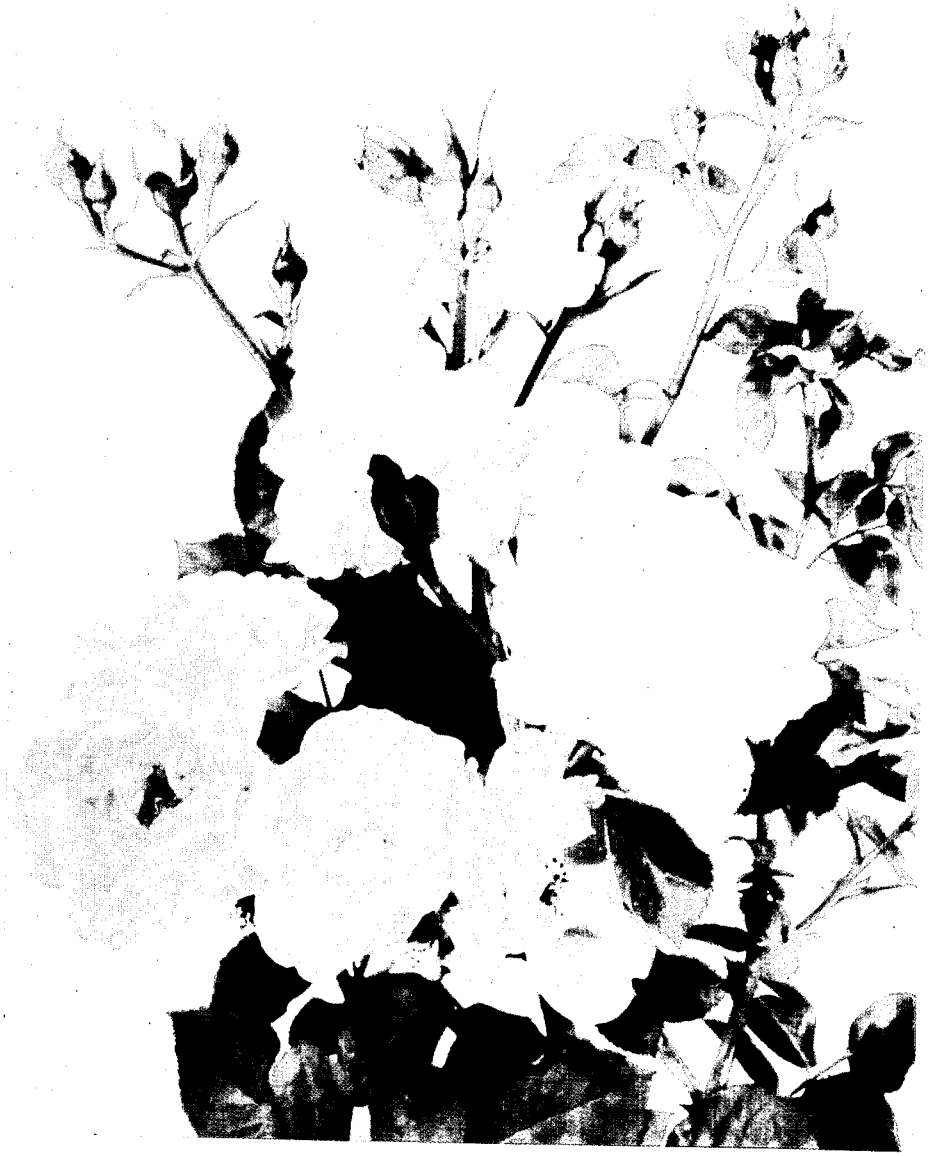
Inventor
H. C. Swim
By: Robb & Robb
Attorneys.

United States Patent Office

Plant Pat. 1,390
Patented May 3, 1955

1,390

ROSE PLANT

Herbert C. Swim, Ontario, Calif., assignor to Armstrong Nurseries, Inc., Ontario, Calif., a corporation of California Application August 23, 1954, Serial No. 451,726

1 Claim. (Cl. 47—61)

The present invention relates to a new and distinct variety of rose plant of the hybrid polyantha class, which was originated by me by crossing two well-known varieties, "World's Fair" (Plant Patent No. 362) and "Pinocchio" (Plant Patent No. 484), the former variety having been used as the seed parent, and the latter variety having been used as the pollen parent.

The primary objective in making this cross was to produce a new and more desirable rose variety which combines the best characteristics of the parent varieties. This objective was fully achieved, as evidenced by the fact that the new variety is characterized particularly as to novelty by a superior cluster blooming habit inherited from its parent "Pinocchio," good petal substance comparable to that of "Pinocchio," with attendant superior lasting qualities of the flowers, good petal-shedding qualities of the old blooms of the new variety, comparable to that of its parent "World's Fair," and the distinctive color of the flowers which range in general color tonality in shades of Coral Pink and Deep Salmon Pink which the pollen parent, "Pinocchio," sometimes gives to its progeny.

In comparison with its seed parent "World's Fair," the bloom color of my new variety is distinctly different and ranges in shades of Coral Pink and Salmon Pink, whereas the blooms of "World's Fair" are a deep shade of red which may be more specifically described as Deep Crimson, fading to Scarlet; the blooms of the new variety are produced in many-flowered clusters, with substantially more flowers per cluster than "World's Fair"; and the petal substance of the new variety is substantially better than that of "World's Fair."

As compared with its pollen parent "Pinocchio," the bloom color of my new variety is somewhat different, since the bloom color of "Pinocchio" is a lighter shade of pink which may be best described as pink-suffused Salmon color; the petals of the old blooms of the new variety shed readily, whereas those of "Pinocchio" tend to persist longer; and the blooms of my new variety have from 20 to 25 petals, whereas those of this parent usually have about 30 petals.

It will be evident from the foregoing that my new variety is definitely distinguished from its parents, as well as from all other varieties of the same class of which I am aware, and asexual reproduction of the new variety by budding, as performed at Ontario, California, shows that the foregoing novel characteristics and distinctions come true to form and are established and transmitted through succeeding propagations.

The accompanying drawing shows typical specimens of the blooms, foliage and stems of my new variety in different stages of development, and as depicted in color as nearly true as it is reasonably possible to make the same in a color illustration of this character.

The following is a detailed description of my new variety, with color terminology in accordance with Robert F. Wilson's Horticultural Colour Chart (hereinafter abbreviated as "Wilson") and Robert Ridgway's Color Standards and Nomenclature (hereinafter abbreviated as "Ridgway"), as indicated;

Type: Bush; outdoor; seedling; for garden decoration.
Class: Hybrid polyantha.
Breeding: Seedling.
*Seed parent.*—"World's Fair."
*Pollen parent.*—"Pinocchio."
Propagation: Holds its distinguishing characteristics through succeeding propagations by budding.

FLOWER

Locality where grown and observed: Ontario, California.
Flowers borne: Usually several to stem; in regular, rounded clusters; on strong stems of medium length.
Quantity of bloom: Abundant, outdors.
Continuity: Nearly continuous during growing season.
Fragrance: Slight.
Bud:
*Peduncle.*—Short; average caliper; erect; moderately smooth; numerous gland-tipped cilia; some hairs. Color—near Biscay Green, Plate XVII (Ridgway), overlaid somewhat with near Indian Red, Plate XXVII (Ridgway), on side exposed to the sun.
*Before calyx breaks.*—Size—medium. Form—from short to medium length; ovoid; with foliaceous appendages; with tomentum and gland-tipped cilia on the surface of the bud; usually without much-cut, foliaceous parts extending beyond the tip of the bud.
*As calyx breaks.*—Color—near Porcelain Rose, Plate 620, page 147 (Wilson).
*Sepals.*—Inner surface has fine, woolly tomentum; margins of alternate sepals lined with fine, woolly tomentum; others lined with gland-tipped cilia.
*As first petal opens.*—Size—average. Form—from short to medium length; ovoid. Color: Outside—between Porcelain Rose, Plate 620/1, page 147 (Wilson) and Carmine Rose, Plate 621/1, page 75 (Wilson); inside—near Porcelain Rose, Plate 620, page 147 (Wilson), shading to near Porcelain Rose, Plate 620/1, page 147 (Wilson) toward base of petal.
*Opening.*—Opens up well; is not retarded from opening by cold, hot, wet or dry weather.
Bloom:
*Size (when fully open).*—Average; from 2½ inches to 3 inches.
*Petalage.*—Semi-double; from 20 to 25 petals, plus 3 to 6 petaloids; arranged regularly.
*Form.*—From flat to somewhat cupped at first, but later becoming open; petals being at first cupped, with lateral margins of inner petals usually reflexed slightly from ¼ to ⅓ of upper portion of petals, and lateral margins of outer petals often reflexed from ½ to ¾ of petal length, with apex of outer petals sometimes reflexed from ⅛ to ¼ of petal length; becoming later at maturity flat-cupped, with lateral margins reflexed usually from ½ to ¾ of petal length, but sometimes reflexed for entire length of the petal, with apex reflexed sometimes from ¼ to ½ of petal length, particularly on outer petals.
Petals:
*Texture.*—Thick; leathery; with inside satiny and outside from shiny to satiny.
*Shape.*—Outside—broadly obovate, with apex flat, and sometimes with 1 or 2 notches. Intermediate—obovate, with apex rounded to flat, and sometimes with 1 or 2 notches. Inside—narrowly obovate, with apex rounded, and with 1 or 2 notches.

This description of a newly opened flower was made from a rose grown outdoors in the month of June, at Ontario, California:

Color:

*Outside petal.*—Outside surface—between Carmine Rose, Plate 621/1, page 75 (Wilson) and Camellia Rose, Plate 622/2, page 148 (Wilson); small area at base of petal near attachment near Aureolin, Plate 3/3, page 3 (Wilson). Inside surface—between French Rose, Plate 520, page 136 (Wilson) and Porcelain Rose, Plate 620/1, page 147 (Wilson); near Porcelain Rose, Plate 620, page 147 (Wilson) around upper margin of petal; small area at base of petal near attachment near Aureolin, Plate 3/3, page 3 (Wilson).

*Intermediate petal.*—Outside surface—between Carmine Rose, Plate 621/1, page 75 (Wilson) and Camellia Rose, Plate 622/2, page 148 (Wilson); small area at base of petal near attachment near Aureolin, Plate 3/3, page 3 (Wilson). Inside surface—between French Rose, Plate 520, page 136 (Wilson) and Porcelain Rose, Plate 620/1, page 147 (Wilson); near Porcelain Rose, Plate 620, page 147 (Wilson) around upper margin of petal; small area at base of petal near attachment near Aureolin, Plate 3/3, page 3 (Wilson).

*Inner petal.*—Outside surface—between Carmine Rose, Plate 621/1, page 75 (Wilson) and Camellia Rose, Plate 622/2, page 148 (Wilson); small area at base of petal near attachment near Aureolin, Plate 3/3, page 3 (Wilson). Inside surface—between French Rose, Plate 520, page 136 (Wilson) and Porcelain Rose, Plate 620/1, page 147 (Wilson); near Porcelain Rose, Plate 620, page 147 (Wilson) around upper margin of petal; small area at base of petal near attachment near Aureolin, Plate 3/3, page 3 (Wilson).

This description was made from a rose that was open for 3 days outdoors in the month of June, at Ontario, California:

Color:

*Outside petal.*—Outside surface—between Camellia Rose, Plate 622/2, page 148 (Wilson) and Neyron Rose, Plate 623/2, page 76 (Wilson); small area at base of petal near attachment near Primrose Yellow, Plate 601/3, page 65 (Wilson). Inside surface—between Dawn Pink, Plate 523/1, page 137 (Wilson) and Camellia Rose, Plate 622/2, page 148 (Wilson); heavily overlaid, particularly on exposed portion of petals towards margins, with between Scarlet, Plate 19/1, page 19 (Wilson) and Geranium Lake, Plate 20/1, page 20 (Wilson); small area at base of petal near attachment near Primose Yellow, Plate 601/3, page 65 (Wilson).

*Inside petal.*—Outside surface—between Camellia Rose, Plate 622/2, page 148 (Wilson) and Neyron Rose, Plate 623/2, page 76 (Wilson); small area at base of petal near attachment near Primrose Yellow, Plate 601/3, page 65 (Wilson). Inside surface—between Dawn Pink, Plate 523/1, page 137 (Wilson) and Camellia Rose, Plate 622/2, page 148 (Wilson); heavily overlaid, (particularly on exposed portion of petals towards margins, with between Scarlet, Plate 19/1, page 19 (Wilson) and Geranium Lake, Plate 20/1, page 20 (Wilson); small area at base of petal near attachment near Primose Yellow, Plate 601/3, page 65 (Wilson).

General color effect:

*Newly opened flower.*—Between French Rose, Plate 520, page 136 (Wilson) and Porcelain Rose, Plate 620, page 147 (Wilson); small area at base of petal near attachment near Aureolin, Plate 3/3, page 3 (Wilson).

*3-days open.*—Between Dawn Pink, Plate 523, page 137 (Wilson) and Camellia Rose, Plate 622/1, page 148 (Wilson); heavily overlaid, particularly on exposed portion of petals towards margins, with between Scarlet, Plate 19/1, page 19 (Wilson) and Geranium Lake, Plate 20/1, page 20 (Wilson); small area at base of petal near attachment near Primrose Yellow, Plate 601/3, page 65 (Wilson).

Behavior: Drop off cleanly; not particularly affected by cold, hot, wet or dry weather.

Flower longevity: On bush in garden—4 days in June. Cut roses grown outdoors and kept at livingroom temperatures—4 days in June.

REPRODUCTIVE ORGANS

Stamens: Many; arranged regularly about pistils.

Filaments: From short to medium length; from 4 to 9 mm. in length; most with anthers.

*Color.*—Between Sulphur Yellow, Plate 1/2, page 1 (Wilson) and Canary Yellow, Plate 2/2, page 2 (Wilson).

Anthers: From medium to large in size; all open approximately at once.

*Color.*—Upper side—margins near Saffron Yellow, Plate 7/2, page 7 (Wilson), with remainder near Aureolin, Plate 3/3, page 3 (Wilson). Under side—margins near Saffron Yellow, Plate 7/2, page 7 (Wilson), with remainder near Aureolin, Plate 3/3, page 3 (Wilson).

Pollen: Moderate abundance.

*Color.*—Between Saffron Yellow, Plate 7/2, page 7 (Wilson), and Cadmium Orange, Plate 8/2, page 8 (Wilson).

Pistils: Average number; approximately 60 in number.

Styles: Moderately even; average length; from 6 to 10 mm. in length; thin; somewhat bunched.

*Color.*—Near Uranium Green, Plate 63/3, page 63 (Wilson), overlaid on upper 1/3 of style with near Carmine, Plate 21/1, page 21 (Wilson).

Stigma:

*Color.*—Between Primose Yellow, Plate 601/2, page 65 (Wilson) and Empire Yellow, Plate 603/2, page 66 (Wilson).

Ovaries: Usually all enclosed in calyx, but with a few sometimes protruding from calyx.

Hips: Average length; ovoid; smooth; walls thick and fleshy.

*Color (1/4 mature).*—Between Calliste Green, Plate VI (Ridgway) and Biscay Green, Plate XVII (Ridgway).

Sepals: Permanent; medium length; recurved.

*Color.*—Inside—between Courge Green, Plate XVII (Ridgway) and Biscay Green, Plate XVII (Ridgway), masked by White woolly tomentum. Outside—between Courage Green, Plate XVII (Ridgway) and Biscay Green, Plate XVII (Ridgway), overlaid with near Neutral Red, Plate XXXVIII (Ridgway).

Seeds: Average number; medium size; from 7 to 12 in number.

PLANT

Foliage:

*Leaves.*—Compound of usually 5 to 7 leaflets; from normal quantity to abundant; medium size; somewhat leathery; semi-glossy.

*Leaflets.*—Shape—ovoid, with apex acute. Base—round. Margin—simply serrate.

*Color.*—Mature: Upper surface—between Forest Green, Plate XVII (Ridgway) and Deep Dull Yellow-Green, (1) Plate XXXII (Ridgway); under surface—near Chromium Green, Plate XXXII (Ridgway). Young: Upper surface—between Chromium Green, Plate XXXII (Ridgway)

and Deep Dull Yellow-Green, (1) Plate XXXII (Ridgway), overlaid along margins with near Neutral Red, Plate XXXVIII (Ridgway); under side—between Turtle Green, Plate XXXII (Ridgway) and Chromium Green, Plate XXXII (Ridgway, overlaid along margins with between Corinthian Purple, Plate XXXVIII (Ridgway) and Neutral Red, Plate XXXVIII (Ridgway).

*Rachis (the supporting stem of the compound leaf).*—Average size. Upper side—grooved, with hairs and some stipitate glands on edges. Under side—smooth, with few, usually 1 or 2, prickles.

*Stipules.*—From medium length to long; medium width; with medium length points turning out at an angle of more than 45°; recurved toward the stem.

*Disease resistance.*—Better than average resistance to mildew, as compared with other varieties grown under comparable cultural conditions at Ontario, California.

Growth:

*Habit.*—Spreading; much-branched.

*Growth.*—Vigorous.

*Canes.*—Medium caliper.

*Main stems.*—Color—between Oil Green, Plate V (Ridgway) and Spinach Green, Plate V (Ridgway). Large prickles—from several to many; medium length; almost straight; with medium length, moderately broad base. Color—between Drab Gray, Plate XLVI (Ridgway) and Light Grayish Olive, Plate XLVI (Ridgway). Small prickles—few. Color—near Light Drab, Plate XLVI (Ridgway). Hairs—none.

*Branches.*—Color—between Light Elm Green, Plate XVII (Ridgway) and Bice Green, Plate XVII (Ridgway). Large prickles—several; medium length; almost straight; with medium length, moderately broad base. Color — near Wood Brown, Plate XL (Ridgway). Small prickles—few. Color—near Wood Brown, Plate XL (Ridgway). Hairs—none.

*New shoots.* — Color — near Biscay Green, Plate XVII (Ridgway), overlaid with between Mineral Red, Plate XXVII (Ridgway) and Deep Corinthian Red, Plate XXVII (Ridgway). Large prickles—several; medium length; almost straight; with medium length, moderately broad base. Color—between Acajou Red, Plate XIII (Ridgway) and Mineral Red, Plate XXVII (Ridgway). Small prickles—few. Color—near Mineral Red, Plate XXVII (Ridgway). Hairs—none.

I claim:

A new and distinct variety of rose plant of the hybrid polyantha class, substantially as herein shown and described, characterized particularly as to novelty by its superior, many-flowered cluster blooming habit, the good petal substance of its flowers and their attendant superior lasting qualities, the distinctive color of its flowers ranging in general color tonality in shades of Coral Pink and Deep Salmon Pink, and the good petal-shedding qualities of its old blooms.

No references cited.